United States Patent
O'Young et al.

[11] Patent Number: 5,695,618
[45] Date of Patent: Dec. 9, 1997

[54] OXIDATIVE COUPLING OF METHANE ON OCTAHEDRAL MOLECULAR SIEVE

[75] Inventors: Chi-Lin O'Young, Poughkeepsie, N.Y.; Yan-Fei Shen, Storrs, Conn.; Mark William Simon, Willington, Conn.; Steven Lawrence Suib, Storrs, Conn.; Richard Paul Zerger, McPherson, Kans.

[73] Assignee: Texaco Inc., White Plains, N.Y.

[21] Appl. No.: 465,691

[22] Filed: Jun. 6, 1995

Related U.S. Application Data

[63] Continuation of Ser. No. 92,103, Jul. 16, 1993, abandoned.
[51] Int. Cl.$^6$ ........................................... C07B 61/00
[52] U.S. Cl. .................... 204/157.43; 204/157.15; 204/157.47; 204/157.6; 204/168; 585/953
[58] Field of Search .................. 204/157.15, 157.43, 204/157.47, 157.6, 168; 585/953

[56] References Cited

U.S. PATENT DOCUMENTS

| | | | |
|---|---|---|---|
| 4,322,394 | 3/1982 | Mezey et al. | 423/244 |
| 5,015,349 | 5/1991 | Suib et al. | 204/168 |
| 5,131,993 | 7/1992 | Suib et al. | 204/168 |

FOREIGN PATENT DOCUMENTS

| | | |
|---|---|---|
| 2535119 | 2/1976 | Germany. |

*Primary Examiner*—Robert J. Hill, Jr.
*Assistant Examiner*—Cybille Delacroix-Muirheid
*Attorney, Agent, or Firm*—Henry H. Gibson; Peter G. Dilworth

[57] ABSTRACT

A method of oxidatively coupling methane onto a manganese oxide molecular sieve comprising:

(a) passing methane through a microwave plasma activation flow reaction zone onto a manganese oxide molecular sieve, whereby polymer-free methane coupled products are produced; and, (b) recovering the polymer-free methane coupled products.

7 Claims, 1 Drawing Sheet

OXIDATIVE COUPLING OF METHANE ON OCTAHEDRAL MOLECULAR SIEVE

This is a continuation of application Ser. No. 08/092,103 filed on Jul. 16, 1993, now abandoned.

BACKGROUND OF THE INVENTION

This invention relates to the oxidative coupling of methane on octahedral molecular sieves, mainly manganese oxides, equivalent to the structures of natural minerals, e.g., todorokite and hollandite.

DISCLOSURE STATEMENT

Hollandite ($BaMn_8O_{16}$), cryptomelane ($KMn_8O_{16}$), manjiroite ($NaMn_8O_{16}$), and coronadite ($PbMn_8O_{16}$) are all naturally occurring manganese minerals with a 3-dimensional framework tunnel structure. The structure consists of $MnO_6$ octahedra which share edges to form double chains, and the octahedra of the double chains share corners with adjacent double chains to form a 2×2 tunnel structure. The size of these tunnels is 4.6 Å×4.6 Å. Ba, K, Na and Pb ions are present in the tunnels and coordinated to the oxygens of the double chains. The identity of the tunnel cations determines the mineral species. The minerals are members of the hollandite-romanechite family which has a common double chain width, T(2×2).

Zeolites and zeolite-like materials are the well-known molecular sieves. These materials use tetrahedral coordinated species $TO_4$, (T=Si, Al, P, B, Be, Ga, etc.,) as the basic structure unit. Through the secondary building units (SBU), a variety of frameworks with different pore structures are then built. Like tetrahedra, octahedra also can be used as the basic structural unit to form octahedral molecular sieves (OMS).

Herein below, we will refer to the materials with a 2×2 tunnel structure as hollandites, and identify each member by the identity of the tunnel ions. Such minerals can be characterized by the general formula:

where A is the counter ion (alkali or alkaline earth metal or $Pb^{+2}$), Mn represents $Mn^{+4}$ and $Mn^{+2}$ and x is 6 to 10 with y varying from 0.1 to 1.3.

Because of their tunnel structure, the materials may be useful as shape selective catalysts and molecular sieves. Although K-hollandite and Ba-hollandite have reportedly been synthesized (as discussed by Parida et al, "Chemical Composition, Microstructure and other Characteristics of Some Synthetic $MnO_2$ of Various Crystalline Modifications", *Electrochimica Acta*, Vol. 26, pp. 435–43 (1981) and Strobel et al, "Thermal and Physical Properties of Hollandite-Type $K_{1.3}Mn_8O_{16}$ and $(K,H_3O)_xMn_8O_{16}$", *J. Solid State Chemistry*, Vol. 55, PP. 67–73 (1984). However, these syntheses are unreliable and considerable difficulties have been experienced by practitioners in this field.

Villa et al discussed the synthesis of oxide systems containing Mn in combination with other elements in "Co—Mn—Ti—K OXIDE SYSTEMS" *Applied Catalysis*, Vol. 26, pp. 161–173 (1986).

Torardi et al. discussed the synthesis of a hollandite-type molybdenum compound ($K_2Mo_8O_{16}$) by hydrothermal reaction of basic $K_2MoO_4$ solutions with Mo metal in "Hydrothermal Synthesis of a new molybdenum hollandite," *Inorganic Chemistry*, Vol. 23.

The hollandites are representative of a family of hydrous manganese oxides with tunnel structures (also described as "framework hydrates") in which Mn can be present as $Mn^{+4}$ and other oxidation states, the tunnels vary in size and configuration, and various mono- or divalent cations may be present in the tunnels. Such cations may serve to form and support the tunnels in some cases. Clearfield describes various hydrous manganese oxides with tunnel structures in "Role of Ion Exchange in Solid-State Chemistry," *Chemical Reviews*, Vol. 88, pp. 125–131 (1988). Pyrolusite or β-$MnO_2$ has tunnels only one $MnO_6$ octahedron square (1×1), or about 2.3 Å square, while in ramsdellite, $MnO_2$, these octahedra form (2×1) tunnels, about 2.73 Å×4.6 Å. Nsutite, γ-MnO2, is described as an intergrowth of pyrolusite and ramsdelite and also has (2×1) tunnels. Psilomelane, $Ba_2Mn_5O_{10}xH_2O$, and romanechite (with $K^{+2}$ substituted for $Ba^{+2}$ in the psilomelane formula) have (3×2) tunnels parallel to the cell b axes, about 4.6 Å×6.9 Å. Todorokites, (Na,Ca,Mn) $Mn_3O_7xH_2O$, have (3×3) tunnels, about 6.9 Å square, and monoclinic cells. Todorokites and other species are described by Turner et al. in "Todorokites: A New Family of Naturally Occurring Manganese Oxides," *Science*, May 29, 1981, pp. 1024–1026, in which it is noted that since todorokites are often found in deep-sea manganese nodules containing high concentrations of copper and nickel, "it seems probable that the smaller transition elements substitute for $Mn^{+2}$ in the octahedral framework." The same article suggests a new partial nomenclature scheme for such manganese oxide structures—T(m,n), in which T donates a tunnel structure and the dimensions of the tunnels are indicated by (m,n). In this notation, the common dimensions responsible for intergrowth (m) is listed first, while (n) represents a variable dimension.

D. C. Golden et al., discloses the synthesis of todorokite in *SCIENCE* 231.717 (1986).

U.S. Pat. No. 5,015,349 discloses a method for cracking a hydrocarbon material. The method includes introducing a stream including a hydrocarbon fluid into a reaction zone. A microwave discharge plasma is continuously maintained within the Reaction zone, and in the presence of the hydrocarbon fluid. Reaction products of the microwave discharge are collected downstream of the reaction zone.

The disclosure of U.S. Pat. No. 5,015,349 is incorporated herein by reference.

Herein below, we will refer to the (3×3) tunnel structure as OMS-1 and the (2×2) tunnel structure as OMS-2.

Many of these tunnel or framework hydrates in addition to the (2×2) hollandites and (3×3) todorokites have potential for use in separations, absorbent materials or catalyst materials. Hence, a use of the present product as a catalyst is desired.

Thus, the object of this invention is to use the materials of this invention as a catalyst to activate methane ($CH_4$) onto coupled hydrocarbons.

SUMMARY OF THE INVENTION

A method of oxidatively coupling methane ($CH_4$) onto a manganese molecular sieve comprising:

(a) passing methane through a microwave plasma activation flow (quartz) reactor onto a manganese oxide catalyst sieve, whereby polymer-free methane coupled products are produced; and (b) recovering the polymer-free methane coupled products.

DETAILED DESCRIPTION OF THE INVENTION

Figure 1:
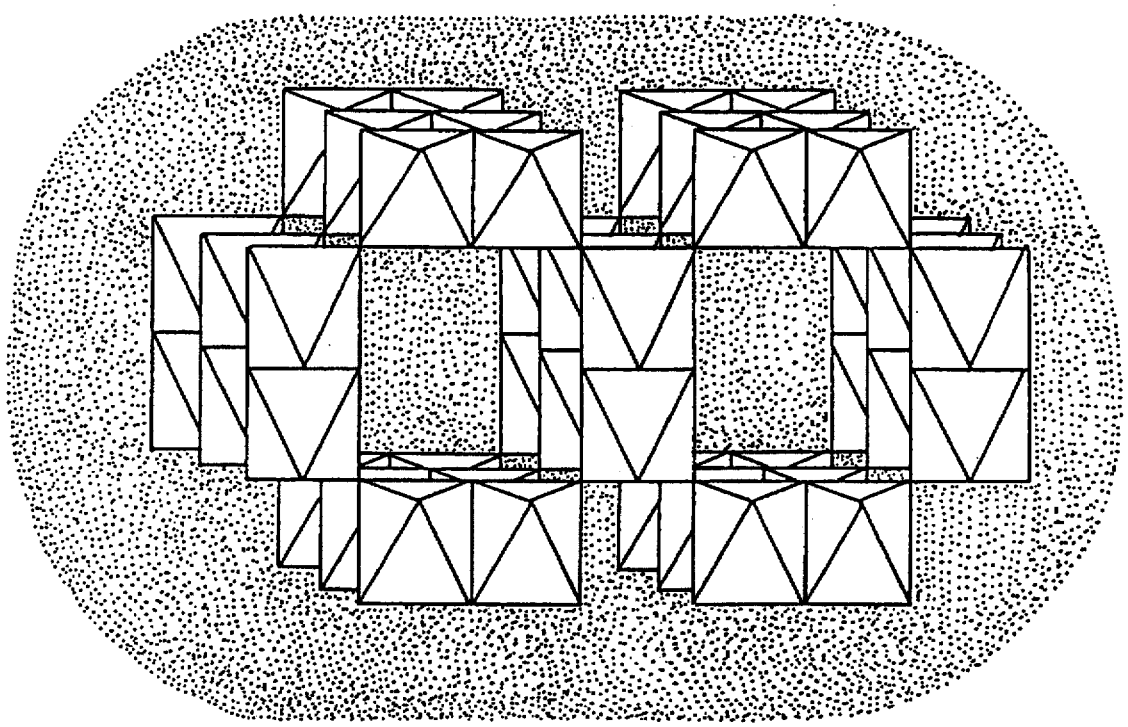
FIG. 1 shows the three-dimensional framework tunnel structures of OMS-2, hollandite (2×2)
Figure 2:
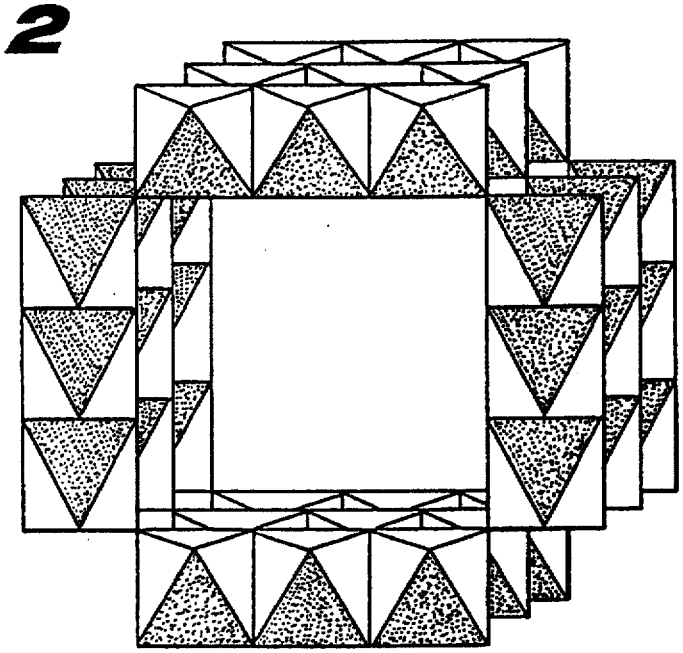
FIG. 2 shows the three-dimensional framework tunnel structure of OMS-1, todorokite (3×3).

According to the present invention, it is possible to crack or activate hydrocarbons such as methane, for example, by breaking C—H bonds using the microwave plasma without a catalyst. However, the ability to control the reaction and produce specific desired end products is generally low in the absence of a catalyst. In other words, the selectivity associated with the reaction is usually low unless a catalyst is provided. Selection of an appropriate catalyst is essential, if high selectivity of the end product and good control of the reaction is to be obtained.

The catalyst should be positioned downstream of the reaction zone. If the catalyst is placed within the plasma reaction zone there is a significant danger that the surface of the catalyst may become prematurely coked. It has been found that the best results are obtained by locating the catalyst just outside the zone in which the microwave plasma is created. The catalyst can be placed within the tubing carrying gases from the reactor outlet. Alternatively, and preferably, the catalyst may be placed within a U-tube downstream of the reactor outlet.

Selection of the catalyst is dependent somewhat on reactants and reaction conditions. Generally, a metal or metal oxide material is employed as the catalyst. If methane is used as the reactant gas, the catalyst must be a hydrogen acceptor if high selectivity towards ethane or ethylene is to be attained. For the production of olefins, it is necessary to use a catalyst that can adsorb hydrogen, such that unsaturated species will result. Typically, dehydrogenation catalysts such as nickel are used for this purpose.

Platinum catalysts are strong oxidizing catalysts. Large amounts of $CO_2$ are formed when Pt is used as a catalyst with the process of the present invention. At the same time, relatively large amounts of HCHO are formed. Conversely, nickel catalysts tend to minimize the formation of highly oxidized species and favor methanol production instead.

To be useful in the present invention, a catalyst should be resistant to coking under low power microwave reaction conditions, and should also be thermally and photochemically stable. Thermal stability refers to the ability of the catalyst to withstand the operating temperatures of the hydrocarbon cracking reactions carried out using the low power microwave energy conditions of the present invention.

In general, to be useful as a catalyst element in the instant process, a composition must withstand continuous long term exposure to temperatures up to about 500° C. Long term exposure refers to the intended duration of operation of the reactor vessel of the invention. It is contemplated that in commercial operation the microwave cracking process of the invention may be conducted continuously for several days, or more before the process is halted for cleaning the reaction vessel. The catalyst element of the invention should be non-volatile under operating conditions. A high catalyst surface area is desirable. A high surface area can be attained by providing the catalyst in a suitable shape or size, e.g. in finely divided powder form. In an alternative arrangement, the catalyst can take the form of a fine mesh screen or a sintered disc. In addition, the catalyst array may be disposed on one or more silica supports that are positioned in the reactant stream.

The following Examples are provided to illustrate the advantages of the present invention.

EXAMPLE 1

Methane Coupling

The detailed apparatus of the microwave plasma activation can be found in the U.S. Pat. No. 5,015,349. In this example, methane was passed through a flow reactor made of quartz having an outside diameter of 12 mm with a flow rate of 60 mL/min and at a total pressure of 20 torr. A Beenaker resonance cavity was used to activate methane. A microwave generator having 60 watts power delivered by the generator was used. The hydrated todorokite catalyst was used as a powder and placed downstream of the plasma zone, about one mm outside the plasma and spread on the bottom of the quartz tube reactor. Products were collected in a cold trap and then directly injected into a gas chromatograph through a gas sampling valve. Products were identified by using known standards and comparison to measured retention times. Gas chromatography method were used to check the identification of some products. The observed conversion of methane of the catalyst was 98.5%. The product distribution included 9.9% ethylene, 17.8% ethane, 9.9% acetylene, 19.6% propane, 22.6% C4 hydrocarbons and 18.6% C5+ hydrocarbons and polymer deposit.

EXAMPLE 2

Todorokite Catalyst

The dehydrated todorokite catalyst was tested with the same procedures, except the methane flow rate was 50 mL/min and the microwave power was 40 watts. The observed conversion of methane for the catalyst was 97.8%. The product distribution included 20% ethylene, 42% ethane, 25% acetylene, 0.2% propane, 1% C4 hydrocarbons and 10% C5 hydrocarbons. No polymer deposit was observed with this catalyst.

As illustrated above, and according to U.S. Pat. No. 5,015,349 and the present invention, it is possible to activate methane using the microwave plasma technique without a catalyst. However, the ability to control the reaction and produce specific desired products is generally low in the absence of a catalyst, i.e., poor selectivity. Selection of an appropriate catalyst is essential, if high selectivity of the end products and good control of the reactions is to be obtained. Both examples have shown that associated with the microwave plasma technique, manganese oxide molecular sieves are active and selective catalysts for the oxidative coupling of methane. The conversion is extreme high (>98%) and the selectivity of C2+ products is also good. The unusual selectivity toward C4 and C5+ products shown in Example 1 should be noted. It is not possible to obtain such selectivities with metal or other metal oxide catalysts. The enhanced coupling may be due to the tunnel structure of the todorokite. The selectivities markedly change as the todorokite is hydrated and then dehydrated.

We claim:

1. A method of oxidatively coupling methane onto a manganese molecular sieve comprising:
   (a) passing methane through a microwave plasma activation flow reaction zone onto a manganese oxide molecular sieve catalyst to produce polymer-free methane coupled products, the products containing ethylene, ethane, acetylene, propane, ($C_4$) hydrocarbons and ($C_5$) hydrocarbons; and,
   (b) recovering said polymer-free methane coupled products.

2. The method of claim 1 wherein the methane passing through said flow reaction zone has a flow rate of between 10 and 500 ml/min and a pressure of between 3 and 760 torr.

3. The method of claim 1, wherein the microwave energy supplied to the reaction zone is adjusted until the concentration of said methane coupled products cannot be increased by further adjustment of said microwave energy.

4. The method of claim 3, wherein the methane passing through said flow reaction zone has a flow rate of between 10 and 500 ml/min and a pressure of between 3 and 760 torr.

5. The method of claim 1, additionally comprising locating the catalyst just outside the zone in which the microwave plasma is created.

6. A method of oxidatively coupling methane onto a manganese molecular sieve comprising:

(a) passing methane through a microwave plasma activation flow reaction zone onto a manganese oxide molecular sieve catalyst wherein said molecular sieve is todorokite, hollandite, or substituted octahedral molecular sieve to produce polymer-free methane coupled products, the products containing ethylene, ethane, acetylene, propane, ($C_4$) hydrocarbons and ($C_5$) hydrocarbons; and, (b) recovering said polymer-free methane coupled products.

7. The method of claim 6 wherein the methane passing through said flow reaction zone has a flow rate of between 10 and 500 ml/min and a pressure of between 3 and 760 torr.

* * * * *